United States Patent
Wang et al.

(10) Patent No.: US 10,544,203 B2
(45) Date of Patent: Jan. 28, 2020

(54) HUMAN FGFR2B EXTRACELLULAR DOMAIN AND NUCLEIC ACID FOR CODING SAME

(71) Applicant: Guangzhou Shenglu Biotech Limited Company, Guangzhou (CN)

(72) Inventors: Ju Wang, Guangzhou (CN); Yi Wang, Guangzhou (CN)

(73) Assignee: Guangzhou Shenglu Biotech Limited Company (CN)

( * ) Notice: Subject to any disclaimer, the term of this patent is extended or adjusted under 35 U.S.C. 154(b) by 386 days.

(21) Appl. No.: 15/106,633

(22) PCT Filed: Dec. 19, 2014

(86) PCT No.: PCT/CN2014/094418
§ 371 (c)(1),
(2) Date: Nov. 9, 2016

(87) PCT Pub. No.: WO2015/090231
PCT Pub. Date: Jun. 25, 2015

(65) Prior Publication Data
US 2017/0152299 A1    Jun. 1, 2017

(30) Foreign Application Priority Data
Dec. 20, 2013  (CN) .......................... 2013 1 0714120

(51) Int. Cl.
C07K 14/705  (2006.01)
C07K 14/71   (2006.01)
A61K 38/17   (2006.01)
A61K 45/06   (2006.01)

(52) U.S. Cl.
CPC ............ *C07K 14/71* (2013.01); *A61K 38/179* (2013.01); *A61K 45/06* (2013.01); *C07K 2319/30* (2013.01)

(58) Field of Classification Search
None
See application file for complete search history.

(56) References Cited

U.S. PATENT DOCUMENTS

| 5,750,371 A * | 5/1998 | Senoo .................... C07K 14/71 |
| | | 435/252.33 |
| 2004/0097493 A1 | 5/2004 | Chen et al. |
| 2010/0196364 A1 | 8/2010 | Kim et al. |
| 2012/0251538 A1 * | 10/2012 | Harding ............... A61K 38/179 |
| | | 424/134.1 |
| 2016/0362496 A1 | 12/2016 | Kim et al. |
| 2017/0152299 A1 | 6/2017 | Wang et al. |

FOREIGN PATENT DOCUMENTS

| CN | 1714093 A | 12/2005 |
| CN | 101139387 A | 3/2008 |
| CN | 102131524 A | 7/2011 |
| CN | 103757026 A | 4/2014 |
| KR | 20110081141 A | 7/2011 |
| WO | 2009101199 A2 | 8/2009 |
| WO | 2013124316 A1 | 8/2013 |

OTHER PUBLICATIONS

International Search Report for Application No. PCT/CN2014/094418 dated Mar. 25, 2015.
Extended European Search Report for European Patent Application No. 14870788.8, dated May 26, 2017.
Celli et al., "Soluble dominant-negative receptor uncovers essential roles for fibroblast growth factors in multi-organ induction and patterning", EMBO Journal, Jan. 1, 1998, pp. 1642-1655, vol. 17, No. 6, Oxford University Press, Surrey, GB, XP002958678, ISSN:0261-4189.
Melnik et al., "Anti-Acne Agents Attenuate FGFR2 Signal Transduction in Acne", Journal of Investigative Dermatology, Mar. 2009, pp. 1868-1877, vol. 129, No. 8, XP 055373654, US ISSN:0022-202X.
Wesche et al., "Fibroblast growth factors and their receptors in cancer", Biochem. J., Jun. 28, 2011, pp. 199-213, vol. 437.
Wang et al., "Antitumor Activity of a Recombinant Soluble Ectodomain of Mutant Human Fibroblast Growth Factor Receptor-2 IIIc", Molecular Cancer Therapeutics, Sep. 2011, pp. 1656-1666, vol. 10, No. 9.
Jiang, Duyin et al.:"The structure and function of the FGFs as signal molecules", Chinese Critical Care Medicine, Apr. 10, 2003, pp. 248-250, vol. 15, No. 4. (Submitted with English Summary.).
Bao, Musheng et al., "The research development of the hFGF2", Foreign Medical Molecular Biology Fascicle, Feb. 28, 2002, pp. 85-87, vol. 24, No. 2. (Submitted with English Abstract).
Melnik et al., "FGFR2 signaling and the pathogenesis of acne", Journal der Deutschen Dermatologischen Gesellschaft, Sep. 2008, pp. 721-728, vol. 6, No. 9.

(Continued)

*Primary Examiner* — Michael D Pak
(74) *Attorney, Agent, or Firm* — Lerner, David, Littenberg, Krumholz & Mentlik, LLP

(57) ABSTRACT

Provided are wild-type, S252W mutant-type, and P253R mutant-type FGFR2b extracellular segments and truncated proteins thereof, coding genes of the foregoing proteins, a recombinant vector comprising the genes, a host cell, a method for preparing the proteins, and a fusion protein of the proteins and an Fc segment. Also provided are applications of the proteins and a composition comprising the proteins in treating eczema, acne, psoriasis, skin allergy, seborrheic dermatitis, or seborrheic alopecia.

1 Claim, 2 Drawing Sheets

Specification includes a Sequence Listing.

(56) References Cited

OTHER PUBLICATIONS

Zheng, Shaojiang et al., "The research development of FGFR signaling and clinical application thereof", Journal of Henan Medical College for Staff and Worders, Aug. 31, 2005, pp. 256-258, vol. 17, No. 4. (Submitted with English Abstract.).

Search Report for Chinese Application No. 201310714120.3, dated Feb. 4, 2015.

Supplementary Search Report for Chinese Application No. 201310714120.3, dated Sep. 11, 2015.

\* cited by examiner

HUMAN FGFR2B EXTRACELLULAR DOMAIN AND NUCLEIC ACID FOR CODING SAME

The present application is a national phase entry under 35 U.S.C. § 371 of International Application No. PCT/CN2014/094418 filed Dec. 19, 2014, published in China, which claims priority from Chinese Patent Application No. 201310714120.3 filed Dec. 20, 2013, all of which are incorporated herein by reference.

TECHNICAL FIELD

The present disclosure relates to the genetic engineering field, particularly to a FGFR2b extracellular fragment, its coding nucleic acid, and use thereof.

BACKGROUND

Inflammatory skin disease refers to redness, swelling, pimple, pustule, and the like on skin, wherein keratinocytes protrude due to cell proliferation, sometime accompanying with itching, which brings great troubles to patients suffering from them. Eczema is a common inflammatory skin disease in epidermis and superficial dermis caused by various internal and external factors, which is generally considered to have some relation with allergy (i.e., allergic reaction). Acne is a chronic inflammatory skin disease involving hair follicle sebaceous gland, generally occurring in the adolescent age, which is commonly called acne vulgaris. Acne is mostly present at sebum excreting sites, such as face, chest, back, and the like, and foreign studies have shown that the acne incidence in the adolescents of 12-24 years old is up to 85%. Recently, scholars worldwide have developed various medicaments for treating the inflammatory skin diseases, including traditional Chinese medicines and Western medicines. At present, the medicaments commonly used in clinic are mainly sterol hormones, antihistamines, and anti-epidermal abnormal keratosis agents such as retinoic acid, but they have high side effects and cannot radically cure these diseases. Keratinocytes are cells on the outmost layer of cells of human body, which prevent the body from external damages. Under pathological conditions, the keratinocytes produce specific immunologically active products and release the proinflammatory cytokines, playing a key role in the inflammatory skin diseases. The interactions between the mesenchymal cells and the epithelial cells activate signal pathways of EGF, FGF, IG and the like are activated when, eventually resulting in the occurrence of inflammation. However, the specific mechanisms thereof are still unclear.

SUMMARY OF THE INVENTION

In view of the above, one purpose of the present disclosure is to provide a FGFR2b extracellular fragment and its coding nucleic acids for treating the inflammatory skin diseases and use thereof.

The present disclosure applies the technical solutions as follows:

1. An isolated protein comprising an amino acid sequence selected from the group consisting of:
    i) amino acid sequences listed in SEQ ID NO: 2, 4, 6, 8, 10, or 12.
2. An isolated protein comprising an amino acid sequence which is selected from the group consisting of the following and has the function of a FGFR2b extracellular fragment:
    ii) an amino acid sequence which is derived from SEQ ID NO: 2, 4, 6, 8, 10, or 12 with deletion, substitution, insertion, and/or addition of one or more amino acids;
    iii) an amino acid sequence which has at least 80% sequence homology with SEQ ID NO: 2, 4, 6, 8, 10 or 12; or
    iv) an amino acid sequence encoded by a nucleic acid capable of hybridizing with a complementary sequence of a nucleic acids encoding the amino acid sequence of SEQ ID NO: 2, 4, 6, 8, 10 or 12 under stringent conditions.
3. The isolated protein according to item 2, wherein the isolated protein is derived from human.
4. An isolated nucleic acid encoding the isolated protein according to any one of items 1 to 3.item
5. A vector comprising the nucleic acid of item 4.
6. A host cell comprising the vector of item 5.
7. The host cell of item 6, wherein the host cell is selected from the group consisting of a CHO cell, an *E. coli* cell, an insect cell, and a yeast cell.
8. A fusion protein consisting of the isolated protein of any one of items 1 to 3 and a human immunoglobulin Fc fragment.
9. Use of the isolated protein of any one of items 1 to 3, the nucleic acid of item 4, the vector of item 5, the host cell of item 6, or the fusion protein of item 8 in preparing a medicament for treating eczema, acne, psoriasis, skin allergy, seborrhoeic dermatitis or seborrheic alopecia.
10. A pharmaceutical composition for treating eczema, acne, psoriasis, skin allergy, seborrhoeic dermatitis or seborrheic alopecia, comprising the isolated protein of any one of items 1 to 3, the nucleic acid of item 4, the vector of item 5, the host cell of item 6, or the fusion protein of item 8, and a pharmaceutically acceptable vector.
11. The pharmaceutical composition of item 10, further comprising a FGFR2b antagonist, wherein the FGFR2b antagonist is one or more of FGF7 antibody, FGF10 antibody, FGFR2b antibody, AZD4547, AP24534, BGJ398, PD173074, NP603, su5402, su6668, PD161570, PD166866, iRNA, microRNA, antisense RNA, spry, MKP3, DUSP, SEF, and XFLRT3.
12. Use of one or more of FGF7 antibody, FGF10 antibody, FGFR2b antibody, AZD4547, AP24534, BGJ398, PD173074, NP603, su5402, su6668, PD161570, PD166866, iRNA, microRNA, antisense RNA, spry, MKP3, DUSP, SEF and XFLRT3 in preparing a medicament for treating eczema, acne, psoriasis, skin allergy, seborrhoeic dermatitis or seborrheic alopecia.

The beneficial effects of the present disclosure include the use of a polypeptide of FGFR2b extracellular fragment or a pharmaceutical composition thereof in inhibiting the occurrence of inflammation by the blockage of the growth factors-mediated signaling pathways of, for example, such as EGF/FGF/VEGF/IGF, and the like. Specially, the present disclosure can inhibit the secretion of sebum and the symptoms of the inflammatory skin diseases, such as redness, swelling, itching, or the like, thus contributing to the improvement of the therapy and restoration of the problematic skins with eczema, allergic dermatitis, skin allergy, seborrheic dermatitis, acne, or the like.

DETAILED DESCRIPTION OF EMBODIMENTS

1. Isolated Protein

Figure 1:
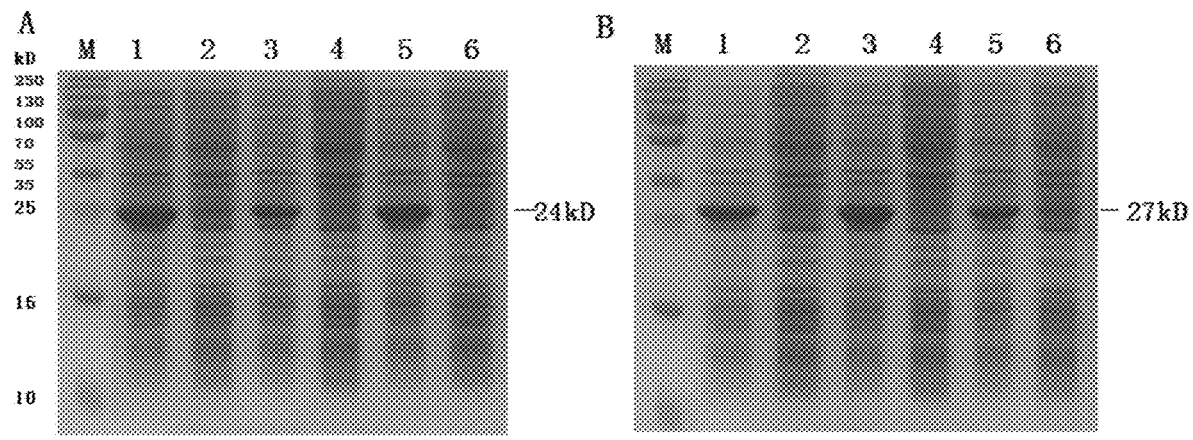
FIG. 1 shows the SDS-PAGE profile of induced expression of 6 types of FGFR2b extracellular fragments according to Example 1. (A) Induced expression profiles of FGFR2b extracellular fragments of wild-type, S252W mutant type, and P253R mutant type of SEQ ID NO.8, 10, and 12. (B) Induced expression profiles of FGFR2b extracellular fragments of wild-type, S252W mutant type, and P253R mutant type FGFR2b extracellular fragments of SEQ ID NO.2, 4, and 6. Lane 1: induced wild type; Lane 2: uninduced wild type; Lane 3: induced S252W mutant-type; Lane 4: non-induced S252W mutant-type FGFR2b extracellular fragments; Lane 5: induced P253R mutant type; Lane 6: uninduced P253R mutant type; and M: molecular weight standard.

In one aspect, the present disclosure provides an isolated protein comprising an amino acid sequence selected from the group consisting of:
  i) amino acid sequences listed in SEQ ID NO: 2, 4, 6, 8, 10, or 12.

In the description herein, preferably, the term "comprise" means "consisting of". A protein consisting of an amino acid sequence of SEQ ID NO: 2 is a wild-type FGFR2b extracellular fragment. A protein consisting of an amino acid sequence of SEQ ID NO: 4 is a S252W mutant-type FGFR2b extracellular fragment. A protein consisting of an amino acid sequence of SEQ ID NO: 6 is a P253R mutant-type FGFR2b extracellular fragment. A protein consisting of an amino acid sequence of SEQ ID NO: 8 is a truncated protein of the wild-type FGFR2b extracellular fragment. A protein consisting of an amino acid sequence of SEQ ID NO: 10 is a truncated protein of S252W mutant-type FGFR2b extracellular fragment. A protein consisting of an amino acid sequence of SEQ ID NO: 12 is a truncated protein of P253R mutant-type FGFR2b extracellular fragment.

The Receptor for Fibroblast Growth Factor (FGF), or FGFR, is a membrane receptor, wherein its extracellular fragment is capable of binding to a specific ligand while the intracellular portion has a tyrosine kinase activity. FGFR can regulate expression of a target gene by binding of the extracellular fragment with a ligand, activating the dimerization and phospolarylation of the ligand and in turn activating a downstream signal. A FGFR2bextracellular fragment, which is the extracellular fragment of the 2b subtype of a FGF receptor, is capable of inhibiting FGF signal by binding to a ligand and thus reducing the effective concentration of the ligand. Inventors have demonstrated that the isolated protein aforementioned has a function of human FGFR2bextracellular fragment. In the present description, "function of a human FGFR2bextracellular fragment" refers to the capability of inhibiting FGF signal by binding to a FGFR receptor, wherein the FGFR receptor refers to FGF7 or FGF10. Whether the "function of a human FGFR2bextracellular fragment" is present can be determined by methods such as those described in the examples.

In addition, the amino acid sequences of SEQ ID NO: 8, 10, and 12 are listed as below, respectively.

```
                                            SEQ ID NO: 8
KRAPYWTNTEKMEKRLHAVPAANTVKFRCPAGGNPMPTMRWLKNGKEFKQ

EHRIGGYKVRNQHWSLIMESVVPSDKGNYTCVVENEYGSINHTYHLDVVE

RSPHRPILQAGLPANASTVVGGDVEFVCKVYSDAQPHIQWIKHVEKNGSK

YGPDGLPYLKVLKHSGINSSNAEVLALFNVTEADAGEYICKVSNYIGQAN

QSAWLTVLPKQQAPGR

SEQ ID NO: 10
KRAPYWTNTEKMEKRLHAVPAANTVKFRCPAGGNPMPTMRWLKNGKEFKQ

EHRIGGYKVRNQHWSLIMESVVPSDKGNYTCVVENEYGSINHTYHLDVVE

RWPHRPILQAGLPANASTVVGGDVEFVCKVYSDAQPHIQWIKHVEKNGSK

YGPDGLPYLKVLKHSGINSSNAEVLALFNVTEADAGEYICKVSNYIGQAN

QSAWLTVLPKQQAPGR

SEQ ID NO: 12
KRAPYWTNTEKMEKRLHAVPAANTVKFRCPAGGNPMPTMRWLKNGKEFKQ

EHRIGGYKVRNQHWSLIMESVVPSDKGNYTCVVENEYGSINHTYHLDVVE

RSRHRPILQAGLPANASTVVGGDVEFVCKVYSDAQPHIQWIKHVEKNGSK

YGPDGLPYLKVLKHSGINSSNAEVLALFNVTEADAGEYICKVSNYIGQAN

QSAWLTVLPKQQAPGR
```

In another aspect, the present disclosure provides an isolated protein, comprising an amino acid sequence which is selected from the group consisting of the following and has the function of a FGFR2b extracellular fragment:
  ii) an amino acid sequence which is derived from SEQ ID NO: 2, 4, 6, 8, 10, or 12 with deletion, substitution, insertion, and/or addition of one or more amino acids;
  iii) an amino acid sequence which has more than 80%, preferably more than 85%, more preferably more than 87.8%, more preferably more than 90%, more preferably more than 95%, more preferably more than 96%, more preferably more than 97%, more preferably more than 98%, more preferably more than 99%, more preferably more than 99.5% sequence homology with SEQ ID NO: 2, 4, 6, 8, 10 or 12; or
  iv) an amino acid sequence encoded by a nucleic acid capable of hybridizing with a complementary sequence of a nucleic acids encoding the amino acid sequence of SEQ ID NO: 2, 4, 6, 8, 10 or 12 under stringent conditions.

Preferably, a variant of the human FGFR2b extracellular fragmentprotein herein is derived from human.

In the variant of the human FGFR2bextracellular fragment protein herein, the amino acid substitution may be a conservative substitution, i.e., substitution of specific amino acid residue(s) with residue(s) with similar physical-chemical characteristics. Non-limited examples of conservative substitution include substitution among amino acid residues with aliphatic groups (e.g., substitution among Ile, Val, Leu, or Ala), substitution among polar residues (such as substitution between Lys and Arg, Glu and Asp, and Gln and Asn), and the like. Variant obtained from deletion, substitution, insertion, and/or addition can be generated by, for example, site-directed mutagenesis of DNA encoding a wild-type protein(see, e.g., Nucleic Acid Research, Vol. 10, No. 20, p.6487-6500, 1982, the full text of which is incorporated herein by reference), or by artificial synthesis of protein. In the present description, "one or more amino acid" refers to amino acid(s) with a magnitude that is able to be involved in deletion, substitution, insertion, and/or addition by methods of site-directed mutagenesis or artificial synthesis, such as, e.g., 1~20 amino acids, preferably 1~15 amino acids, more preferably 1~10 amino acids, more preferably 1~8 amino acids, more preferably 1~2 amino acids, and even more preferably, 1 amino acid.

The % homology of two amino acid sequences can be determined visually or by mathematical calculation. Or, the % homology of two peptide sequences can be determined by sequence alignment analysis using the GAPcomputer program based on the algorism by Needleman, S. B. and Wunsch, C. D. (J. Mol. Bol., 48: 443-453, 1970) and available from the University of Wisconsin Genetics Computer Group (UWGCG). The default parameters optimized in the GAP program includes: (1) score/matrix blosum62 described by Henikoff, S. and Henikoff, J. G. (Proc. Natl. Acad. Sci. USA, 89:10915-10919, 1992); (2) deduction of 12 points for one gap; (3) deduction of another 4 points for a successive gap; and (4) no deduction of points for a terminal gap. Other programs for sequence alignment analysis used by a person skilled in the art may be used herein. As for the % homology, sequence information can be compared and determined using BLAST program as described in Altschul et al. (Nucl. Acids. Res., 25, p. 3389-3402,1997). This program is available at the website of National Center for Biotechnology Information (NCBI) or DNA Data Bank of Japan (DDBJ). Detailed description of various conditions (parameters) for homology search using BLAST program can also be found on such websites. While the settings can be partially varied as needed, the search is typically performed with default parameters. In addition, % homology of two amino acid sequences can also be determined with programs such as genetic information processing software GENETYX Ver.7 (GENETYX), or FASTA algorism, or the like, in which search may also be performed with default parameters.

In the present description, the term "stringent conditions" refers to the conditions in which the so-called specific hybrids are formed while no non-specific hybrid is formed. Under such conditions, highly homologous DNAs will hybrid with each other. For example, DNAs of no less than 80% homology, preferably no less than 90% homology, more preferably no less than 95% homology, even more preferably no less than 97% homology, and most preferably no less than 99% homology, will hybrid with each other, while DNAs with lower homology than the above mentioned percentages will not. Or, "stringent conditions" may refer to typical Southern hybridization washing conditions, i.e., conditions of washing once or preferably 2 or 3 times, with salt concentration and temperatures of 1×SSC, 0.1% SDS at 60° C., and preferably, 0.1×SSC, 0.1% SDS at 60° C., and more preferably, 0.1×SSC and 0.1% SDS at 68° C.

2. Isolated Nucleic Acid

In another aspect, the present disclosure provides an isolated nucleic acid encoding the FGFR2bextracellular fragment protein above or a variant thereof.

The isolated nucleic acid may be single-stranded or double-stranded, and may be a DNA or RNA or a hybrid of DNA and RNA.

The isolated nucleic acid may be prepared by means of artificial synthesis or by means of, e.g., genetic engineering.

Typically, the amino acid sequences listed in the above SEQ ID NO: 2, 4, 6, 8, 10, or 12 may be encoded, respectively, by a base sequence shown in SEQ ID NO: 1, 3, 5, 7, 9 or 11.

3. Vector and Host Cell

In another aspect, the present disclosure provides a vector comprising said nucleic acid.

There is no particular limitation on the type of vectors, which may be those commonly used by a person skilled in the art. Examples of a vector can be a plasmid, phage, an animal virus, and the like.

In yet another aspect, the present disclosure provides a host cell comprising the vector.

There is no particular limitation on the type of host cells, which may be those commonly used by a person skilled in the art. Examples of a host cells can be a CHO cell, an *E. coli* cell, an insect cell, a yeast cell, and the like.

4. Fused Protein

In another aspect, the present disclosure provides a fusion protein of the FGFR2bextracellular fragment protein as above or a variant thereof and a human immunoglobulin Fc fragment.

5. Pharmaceutical Composition and Use in Pharmacy Thereof

In another aspect, the present disclosure provides a pharmaceutical composition comprising the FGFR2bextracellular fragment protein or a variant thereof, or the nucleic acid, or the vector, or the host cell, or the fusion protein, as an active ingredient, and a pharmaceutically acceptable vector. The pharmaceutical composition disclosed here may be used for treating eczema, acne, psoriasis, skin allergy, seborrhoeic dermatitis or seborrheic alopecia. Examples of a pharmaceutically acceptable vector may include sterile water, physiological saline, vegetable oils, emulsifiers, suspending agents, surfactants, stabilizers, flavoring agents, excipients, vehicles, preservatives, binding agents, and the like.

In another aspect, the present disclosure provides use of the FGFR2bextracellular fragment protein or a variant thereof, or the nucleic acid, or the vector, or the host cell, or the fusion protein, in preparing a medicament for treating eczema, acne, psoriasis, skin allergy, seborrhoeic dermatitis or seborrheic alopecia.

The researches by inventors have shown that each of the FGFR2bextracellular fragment proteins can effectively bind with a FGFR ligand and inhibit FGFR phosphorylation. On the other hand, it is known that Receptor for Fibroblast Growth Factor (FGF), or FGFR, is a membrane receptor, wherein its extracellular fragment is capable of binding to a specific ligand while the intracellular portion has a tyrosine kinase activity. FGFR can regulate expression of a target gene by binding of the extracellular fragment with a ligand, activating the dimerization and phospolarylation of the ligand and in turn activating a downstream signal. Therefore, it can be deduced that, by binding to a FGFR ligand to inhibit the same from binding with membrane FGFR, each of the FGFR2bextracellular fragments can inhibit the activation of downstream signals, which may be associated with the occurrence of inflammatory skin diseases.

Therefore, according to the research results of inventors, it can be concluded that any antagonist of FGFR2b can be used for treating inflammatory skin diseases. In the present specification, antagonists of FGFR2b include, but not limited to, one or more of FGF7 antibody, FGF10 antibody, FGFR2b antibody, AZD4547, AP24534, BGJ398, PD173074, NP603, su5402, su6668, PD161570, PD166866, iRNA, microRNA, antisense RNA, spry, MKP3, DUSP, SEF, and XFLRT3.

The inflammatory skin diseases herein include, but not limited to, eczema, acne, psoriasis, skin allergy, seborrhoeic dermatitis or seborrheic alopecia.

EXAMPLES

For clear understanding of the techniques of the present disclosure, the following examples of embodiments are discussed by way of example with reference to the drawings. It should be understood that such examples are only for the purposed of illustration of the present disclosure, without limiting its scope in any way. Specific experimental conditions, if not explicitly stated in the following examples, typically follow the conventional conditions, such as conditions described by Sambrook et al. in Molecular cloning: A Laboratory Manual (New York: Cold Spring Harbor Laboratory Press, 1989), or as recommended by the manufacturer. The various chemicals used in the examples are all available commercially.

Example 1

Expression of Genes Encoding Polypeptides of Wild-Type and Mutant-Type FGFR2bextracellular Fragments in E. coli This example describes a method for preparing genes encoding wild-type and mutant-type FGFR2b extracellular fragments (SEQ ID NO.1 and 7, SEQ ID NO.3 and 9, and SEQ ID NO.5 and 11), and a method for preparing FGFR2bextracellular fragments (SEQ ID NO.2 and 8, SEQ ID NO.4 and 10, and SEQ ID NO.6 and 12) by expressing such genes in E. coli.

I. Preparation of Genes Encoding FGFR2bextracellular Fragments:

1. Wild-type FGFR2bextracellular fragment total mRNA was extracted from human placenta tissue (fresh placenta tissue, obtained from a hospital in Guangdong Province, China, with consent of the puerpera) using the Trizol method, based on which a cDNA library was established.

(1) Extraction of mRNA Using the Trizol Method:

Cells were incubated until a confluence of 90% and then lysed with addition of Trizol solution. The cell lysis solution obtained was transferred to a EP tube, to which a ⅕ volume of chloroform was added. The colorless aqueous phase in the upper layer was transferred to a new EP tube, to which a ½ Trizol volume of isopropanol was added;

Centrifugation was performed, after which white emulsion-like precipitate was seen at the bottom of the EP tube. Then 75% ethanol was added to wash the precipitate;

After air drying, RNAse-free water was added. Mixing was performed by repeatedly pipetting to allow full dissolution of RNA. RNA concentration and purity was then determined.

(2) Preperation of cDNA by mRNA Reserve Transcription with PCR:

The mRNA sample was added to a PCR tube and pre-denatured in a PCR instrument under 65° C. for 10 min Pre-denatured mRNA sample was immediately placed into ice.

Reverse transcription reaction system: a total volume of 20 μL, and was further added with the following amounts of

| | |
|---|---|
| a, Pre-denaturation: Total RNA | 1 μg |
| DEPC water | up to 11.5 μL |
| b, Reverse transcription Oligo dT | 1 μL |
| 10 mM dNTP | 2 μL |
| HRP RNase inhibitor | 0.5 μL |
| 5 × RT buffer | 4 μL |
| Reverse transcriptaseAce | 1 μL |
| Total volume: | 20 μL |
| Reverse transcription PCRprogram: | 30° C., 10 min; 42° C., 1 h; 70° C., 10 min. |

2. Primer Design:

The primer designs herein are all available from Beijing LiuheHuada Gene Technology Co., Ltd.

Wild-type primer sequences:
```
                                        SEQ ID NO. 13
F1:   CG CATATG GCACCATACTGGACCAAC;

SEQ ID NO. 14
R1:   AT GGATCC CTATTA CAGGATGACTGTTACCAC, including Restriction Enzyme cleavage sites
      Nde I and BamH I.
                                        SEQ ID NO. 15
F1':  CG CATATG AAGAGAGCACCATACTGG;

SEQ ID NO. 16
R1':  AT GGATCC CTATTA TCTTCCAGGCGCTTGCTG, including Restriction Enzyme cleavage
      sites Nde I and BamH I.
```

To obtain genes of S252W mutant-type and P253R mutant-type FGFR2bextracellular fragment polypeptides, two pairs of primers for site-directed mutagenesis were designed, wherein:

```
S252W mutant-type primer sequences are:
                                        SEQ ID NO. 17
F2:   TTGT GGAGCG ATGGCCTCACCGGCCCAT;

SEQ ID NO. 18
R2:   ATGG GCCGGT GAGGCCATCGCTCCACAA₀

P253R mutant-type primer sequences are:
                                        SEQ ID NO. 19
F3:   TTGTGGAGCGATCGCGTCACCGCCCAT;

SEQ ID NO. 20
R3:   ATGGGCGGTGACGCGATCGCTCCACAA
```

3. Amplification of the Gene Sequence of FGFR2b Extracellular Fragment:

To amplify the gene of the wild-type FGFR2bextracellular fragment, the wild-type PCR primer was used to perform a preliminary amplification of the DNA sequence encoding FGFR2bextracellular fragments.

To amplify the two genes of the mutant-type FGFR2b extracellular fragment, the wild-type FGFR2bgene was used as a template in an overlap extension PCR method, with respective mutant-type PCR primers, to obtain the mutant-type FGFR2bextracellular fragment gene with a S252W mutation and the mutant-type FGFR2bextracellular fragment gene with a P253R mutation.

The amplification system and reaction conditions of the gene sequences of the FGFR2bextracellular fragments were as follows(PrimerSTAR max, TaKaRa),

| PCR reaction system: | | Reaction conditions: | | |
|---|---|---|---|---|
| PrimerSTAR max | 25 μL | 96° C. | 5 min | |
| Upstream primer | 3 μL | 94° C. | 15 s | |
| Downstream primer | 3 μL | 60° C. | 15 s | 31 cycles |
| Template | 4 μL | 72° C. | 5 s | |
| ddH20 | 15 μL | 72° C. | 10 min | |
| Total volume | 50 μL | | | |

4. Collection, Purification, and Identification:

Agarose gel electrophoresis and gel extraction were performed. DNA fragments recovered could be determined for the concentrations and purities thereof by agarose gel electrophoresis and UV spectrophotometer. The OD260/OD280 ratio should be 1.7-1.9.

II. Construction of Recombinant Vector for the Wild-Type and Mutant-Type FGFR2bextracellular Fragment Protein Genes.

1. Construction of Recombinant Plasmid by Double Digestion and Ligation Reaction PCR-amplified sequences, along with pET3c vector (Invitrogen, USA) were subjected to double digestion with Nde I and BamH I under the digestion conditions of 37° C. water bath for 4 h;

After the double digestion with Nde I and BamH I, the pET3c plasmid and FGFR2b were ligated under the ligation conditions of 16° C. water bath for 12 h.

2. Expression and Identification of Recombinant Plasmid:

E. coli DH5α strain was transformed by the $CaCl_2$ method:

(1) A DH5α strain with no plasmid was activated, 50 μL of which was then inoculated in a 5 ml LB tube, incubated for 2 h with no antibiotic under 37° C. and shaking. 1.5 ml of cells were collected with centrifugation at 6000 rpm for 1 min;

(2) The supernatant was discarded and the cells were re-suspended with 800 μL ice-bathed $CaCl_2$. The supernatant was again discarded after centrifugation at 6000 rpm for 1 min;

(3) Cells were re-suspended with 50 μL ice-bathed $CaCl_2$ and cells attached to the tube wall were detached by gently pipetting;

(4) 10 μL ligation product was mixed with 50 μL competent cells and place in an ice-bath for 30 min;

(5) The mixture was heat shocked for 90 s under 42° C. and quickly placed on ice for 2-3 min;

(6) 200 μL LB medium was added and mixed well before incubation under 37° C. and shaking at 130-150 rpm for 45 min 3. Identification of Recombinant Plasmid by Dual-Enzyme Digestion:

Multiple single colonies were transferred to LB medium with 0.1%Amp using an inoculating loop, labeled, and incubated under 37° C. and shaking for 12 h. Afterwards, the plasmid was extracted (according to the operational protocol of Omega Plasmid Mini Kit) for identification by dual-enzyme digestion (the same as in Example 1). Monoclones identified by dual-enzyme digestion were sent to Sango Biotech Co., Ltd for sequencing. Six recombinant plasmids with correct sequence confirmed by sequencing were obtained, designated as pET3c-FGFR2b, pET3c-S252W-FGFR2b, and pET3c-P253R-FGFR2b.

III. Expression of Gene of FGFR2bextracellular Fragment Protein in E. coli:

(1) According to the transformation of E. coli DH5α strain using the $CaCl_2$ method as discussed above, each of the six recombinant plasmids was transformed into BL21(+) engineered strain to generate an expression strain;

(2) The BL21(+) engineered strain was inoculated at an inoculation rate of 1:50 to sterilized LB liquid medium containing 0.1%Amp and incubated under 37° C. and shaking (200 rpm);

Control groups and induction groups were established when the cells have reached an OD 600 of 0.6~0.8:

Induction group: 0.84M IPTG was added until a final concentration of 0.84 mM and incubated under 37° C. for induced expression for 3 h;

Control group: no treatment at all; and

The expression status of target protein was identified with SDS-PAGE electrophoresis (See FIG. 1).

Figure 2:
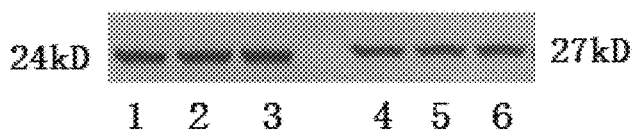
FIG. 2 shows the Western blotting analysis of 6 types of FGFR2b extracellular fragments according to Example 1. 1-3: wild-type, S252W mutant-type, and P253R mutant-type FGFR2b extracellular fragments of SEQ ID NO.8, 10, and 12, respectively; 4-6: wild-type, S252W mutant-type, and P253R mutant-type FGFR2b extracellular fragments of SEQ ID NO.2, 4, and 6, respectively; and M: molecular weight standard.

IV. Collection and Purification of Polypeptides of FGFR2bextracellular Fragment:

(1) After 5 hours of incubation, cells were harvested by centrifugation;

(2) The cells were subjected toultrasonication with the ratio of cell mass to breaking buffer being 1:8~1:10, the breaking buffer being 0.15M NaCl, 25 mM PB, and 2 mM EDTA, with pH=7.5;

(3) In some strains with prokaryotic expression, the FGFR2bextracellular fragment protein was expressed as an inclusion body. In such case, FGFR2bextracellular fragment protein in the active form was obtained by washing of inclusion body and denaturation and renaturation techniques (see the patent ZL200710029286.6 for detailed methods);

(4) Detection was done using Western Blot method, with the Bek antibody (c-17) (Santa Cruz Biotechnology) as a primary antibody and the rabbit secondary antibody (cat NO. AS006,Asbio) as the secondary antibody. The results were shown in FIG. 2, indicating that analogues of FGFR2bextracellular fragments can be specifically recognized by FGFR antibodies.

Example 2

Expression of FGFR2b Extracellular Fragments in Mammalian Cells

This example describes a method for preparing potentially glycosylated polypeptides of FGFR2bextracellular fragment by recombinant expression of wild-type and mutant-type genes of FGFR2bextracellular fragments (SEQ ID NO.1 and 7, SEQ ID NO.3 and 9, and SEQ ID NO.5 and 11) in mammalian cells.

1. Primer Design:

```
                                        SEQ ID NO. 21
F4:  ATAT GGATCC GCCGCCACC ATG GCACCATACTGGACCAAC;

SEQ ID NO. 22
R4:  GCGCAAGCTT TCATTA CAGGATGACTGTTACCAC, including Enzyme cleavage sitesBamH I and
     Hind□.
```

-continued

```
                                    SEQ ID NO. 23
F4':    ATAT GGATCC GCCGCCACC ATGAAGAGAGCACCATACTGG;

SEQ ID NO. 24
R4':    GCGCAAGCTT TCATTA TCTTCCAGGCGCTTGCTG, including Enzyme cleavage sitesBamH I and
        HindIII.
```

2. Vector Construction:

Vector pCDNA3.1(-) (purchased from Invitrogen) was used as the expression vector;

FGFR2b (SEQ ID NO.1 and 21, SEQ ID NO.3 and 9, and SEQ ID NO.5 and 11) were ligated to pCDNA3.1 (using a method same as Example 1) respectively to generate a vector designated as pCDNA3.1-FGFR2b.

3. Transfection of 293 Cells with pCDNA3.1-FGFR2b (1) Six types of recombinant plasmids of pCDNA3.1-FGFR2b were extracted according to the protocol of EndoFree Mini Plasmid Kit (purchased from OMEGA);

(2) Human 293 cells(ATCC CCL1573) were selected as host hells and incubated until confluence in DMEM medium added with fetal bovine sevium and, optionally, nutrients and/or antibiotics in a saturated humid incubator of 37° C. and 5% $CO_2$;

(3) 24 hours prior to the transfection, the 293 cells in their logarithmic phase of growth were digested with 0.25% trypsinase, suspended with antibody-free DMEM medium by pipetting the cells, and transferred into 6-well plates with $2 \times 10^5$ per well. The cells were allowed to reach full adhesion and a cell density of 50%-60%;

(4) Transfection was performed with LipofectamineTM2000 Liposomal Transfection Kit (purchased from Invirtogen, USA) with the following specific steps:

Dilution of LipofectamineTM2000: 5 μL LipofectamineTM2000 per well was added to 250 μL opti-MEM per well in the 6-well plate and stand for 5 min;

Dilution of plasmids to be transfected: dilution was performed by adding 4 μg plasmid to be transfected to 2504, opti-MEM per well in the 6-well plate;

Equal volumes of the above two dilutions were mixed and allowed to stand for 20 min 500 μL of the mixture and 1.5 ml opti-MEM were added to each well; incubation was performed in an incubator of 37° C. and 5% $CO_2$ for 4-6 hours before replacing the medium with 10% FBS DMEM medium; and, 24 h post transfection, the old medium was removed carefully and replaced with fresh DMEM Complete Medium to continue with the incubation.

4. Purification and Identification of FGFR2b Extracellular Fragment Proteins:

The culture was centrifuged at 4° C. and 18000 rpm and the supernatant was collected, the purification steps of the proteins comprising:

A heparin affinity column (GE 17-0998-01 50 ml) was used, which was washed with 3× column volume of double distilled water and then balanced with equilibrium liquid for affinity chromatography; the flow rate was 5 ml/min; after balancing of at least 3× column volume, the supernatant obtained from step 2 was loaded before further washing with 3× column volume of affinity chromatography equilibrium liquid and eluting with heparin eluent; and, the single elution peak was recovered at wavelength of 280 nm to obtain the polypeptides of the wild-type FGFR2b, the S252W mutant-type FGFR2b, and the P253R mutant-type FGFR2b, stored under −70° C. until further analysis.

Equilibrium liquid for affinity chromatography: 25 mM HEPES, 0.15M NaCl, pH=7.5;

Heparin eluent:25 mM HEPES, 1.5M NaCl, pH=7.5; Flow rate: 5 ml/min

Identification using Western Blot shows that FGFR2b extracellular fragment proteins can be specifically recognized by FGFR antibodies.

Example 3

Expression of FGFR2b Extracellular Fragments in CHO Cells

This example describes a method for preparing FGFR2b extracellular fragment genes (SEQ ID NO.2 and 8, SEQ ID NO.4 and 10, and SEQ ID NO.6 and 12) by expressing the wild-type and mutant-type FGFR2b extracellular fragment genes (SEQ ID NO.1 and 7, SEQ ID NO.3 and 9, and SEQ ID NO.5 and 11) in CHO cells. Please refer to Example 1 for the preparation of gene sequences used herein.

1. Primer Design:

```
                                    SEQ ID NO. 25
F5:     ATAT GAATTC GCCGCCACC ATG GCACCATACTGGACCAAC;

SEQ ID NO. 26
R5:     GCGC GGATCC TCATTA CAGGATGACTGTTACCAC, including Enzyme cleavage sitesBamH I and
        EcoRI;

SEQ ID NO. 27
F5':    ATAT GAATTC GCCGCCACC ATGAAGAGAGCACCATACTGG;

SEQ ID NO. 28
R5':    GCGC GGATCC TCATTA TCTTCCAGGCGCTTGCTG, including Enzyme cleavage sites BamH I and
        EcoRI.
```

2. Vector Construction:

Vector pIRESneo3 (purchased from Clontech) was used as the expression vector;

FGFR2b (SEQ ID NO.1 and 7, SEQ ID NO.3 and 9, and SEQ ID NO.5 and 11) were ligated to pCDNA3.1(using a method same as Example 1) respectively to generate six types of vectors designated as pIRESneo3-FGFR2b.

3. Transfection of CHO-DG44 Cell with pIRESneo3-FGFR2

(1) Plasmids pIRESneo3-FGFR2b were extracted according to the protocol of EndoFree Maxiprep Plasmid Kit (Invitrogen);

(2) Chinese hamster ovary cells CHO-DG4 (Invitrogen) were transfected with each of the plasmids from step (1) with the same transfection steps as Example 2 and selected for stably cloned recombinant CHO cells by high-pressure screening with puromycin (400 ng/ml);

(3) The recombinant CHO cells were plated at $5 \times 10^5$ cells/ml in pro CHO5 medium (4 mmol/L glutamine, 0.68 mg/L hypoxanthine, 0.194 mg/L thymidine), 1.5 L of which was incubated for 72 h in a 5 L shake flask at 110 r/min 37° C. and then for another 216 h at 31° C.;

(4) The supernatant of the 1.5 L cell culture was collected, 500 ml of which was then filtered with 0.45 um filter and purified for the target protein with a heparin affinity column.

Example 4

Expression of FGFR2b Extracellular Fragments in Yeast Cells

This example describes a method for preparing wild-type and mutant-type FGFR2b extracellular fragment genes (SEQ ID NO.1 and 7, SEQ ID NO.3 and 9, and SEQ ID NO.5 and 11), and a method for preparing the polypeptides of FGFR2b extracellular fragments (SEQ ID NO.2 and 8, SEQ ID NO.4 and 10, and SEQ ID NO.6 and 12) by expressing the same in yeast cells.

1. Primer Design:

```
Upstream primer F6:
                                SEQ ID NO. 29
5'-ATAT CTCGAG GCCGCCACC ATGGCACCATACTGGACCAAC-3', whereas the Xho I Enzyme Cleavage Site is
underlined;

Downstream primer R6:
                                SEQ ID NO. 30
5'-GCGC TCTAGA TCATTA CAGGATGACTGTTACCAC C -3', whereas the Xba I Enzyme Cleavage Site is
underlined;

Upstream primer F6':
                                SEQ ID NO. 31
5'-ATAT CTCGAG GCCGCCACC ATGAAGAGAGCACCATACTGG-3', whereas the Xho I Enzyme Cleavage Site is
underlined;

Downstream primer R6':
                                SEQ ID NO. 32
5'-GCGC TCTAGA TCATTA TCTTCCAGGCGCTTGCTG -3', whereas the Xba I Enzyme Cleavage Site is
underlined;
```

2. Vector Construction:

Pichia expression vector pPICZαA (Invitrogen) was used.

The operational procedure is the same as Example 1, with F6 and R6 as the primers and Xho I and Xba I as the enzymes. The vectors generated as such were designated as pPICZαA-FGFR2b.

3. Transformation and Identification of E. coli Cells:

E. coli DH5α cells were transformed using the $CaCl_2$ method as in Example 1 to transfer the pPICZαA-FGFR2b into E. coli DH5α cells, respectively. The transformed DH5α cells were subjected to a preliminary screening in a LB plate with Zeocin (100 μg/ml) antibiotic. Single colonies grown on the plate were selected for culturing under 37° C. and shaking at 220 rpm, after which a small amount of plasmid was extracted and identified by restriction enzyme analysis (identification by dual-enzyme digestion with XhoI and Xba I), wherein the positive clones were picked out and sent for sequencing.

4. Transformation of Yeast X33 Cells:

Purified plasmids (each of pPICZαA-FGFR2b) were linearized by Sac I enzyme digestion (digestion system: 10×buffer 2 μl, plasmid 10 μl, Sac I 1 μl, filled with $ddH_2O$ up to 20 μl). Pichia X33 competent cells were electrotransformed respectively as follows: 80 μl X33 competent cells and 20 μl linearized plasmids were mixed evenly, transferred to a pre-cooled electric shock cuvette with 0.2 cm gap, kept on ice bath for 5 min, and electrotransformed with a transformation voltage of electric pulse energy of 1800V for 4.3 ms; 1 ml pre-cooled 1M sorbitol was immediately added to the cuvette and mixed by gently pipetting before transferred to a 1.5 mL EP tube and plated to Hypertonic Complete Medium (YPDS) containing 100 μg/ml Zeocin in a plate; and, the mixture was incubated for 2~3 d under 28° C.

5. Identification and Induced Expression of Recombinant Strains:

Specific procedure can be found in the description of expression of the fused antibody ScFv-Fc by Wang et al. (Construction of a general expression vector for fused antibody ScFv-Fc, China Biotechnology. 2011,31(8):110-117).

6. Purification and Identification of FGFR2b Extracellular Fragment Proteins:

(1) Yeast cells were removed from the fermentation medium by centrifugation;

(2) The recombinant FGFR2b extracellular fragment proteins were subjected to preliminary isolation and purification by using an 8000KD column ultrafilter to concentrate the medium;

(3) The concentrate comprising the FGFR2b extracellular fragment proteins were further purified with heparin affinity column chromatography (the same as Example 2) and identified by Western Blot. The results show that each of the FGFR2b extracellular fragment analogues can be specifically recognized by the FGFR antibodies.

Example 5

Expression of FGFR2b Extracellular Fragments in Baculovirus and Infected Insect Cells This example describes a method for preparing wild-type and mutant-type FGFR2b extracellular fragment genes (SEQ ID NO.1 and 7, SEQ ID NO.3 and 9, and SEQ ID NO.5 and 11), and a method for preparing the polypeptides of FGFR2b extracellular fragments (SEQ ID NO.2 and 8, SEQ ID NO.4 and 10, and SEQ ID NO.6 and 12) by expressing the same in yeast cells.

1. VectorsspFastBac-FGFR2b, pFastBac-FGFR2b-S252W, and pFastBac-FGFR2b-P253R were obtained by the methods described in Example 2 (the same primers as in Example 2 and the vector pFastBac was from Invitrogen).

2. Transformation of competent E. coli DH10Bac cells

Competent E. coli DH10Bac cells (from Invitrogen) stored under −80° C. were thawed on ice; 5 μL plasmid was added to the competent E. coli DH10Bac cells in sterile conditions, kept on ice for 30 min, heat shocked at 42° C. for 45 s, and immediately placed back on ice for 2 min standing; the cells were added with 0.9 ml room-temperature S.O.C. medium (Cat.No.15544-034) and shook for 45 min at 225 rpm (37° C.); the culture was diluted with S.O.C. medium at 1:10, and 100 μL of the diluted culture was placed on a LB plate with 50 μg/ml kanamycin, 10 μg/ml tetracycline, 7 μg/ml (gentamicin, 200 mg/ml IPTG, and 20 mg/mL X-gal, which was then incubated under 37° C. for 24 h; on the next day, white spots were picked for culturing in LB liquid medium with 50 μg/ml kana and the culture was subjected to identification by PCR assay; the identified culture was inoculated in 5 ml medium and incubated under 37° C. overnight; and, the positive rod granules were extracted. The recombinant plasmid DNA was extracted with Bac-to-bac HT Vector kit (purchased from Invitrogen, Cat.1058-027) and agarose gel electrophoresis was performed to detect the transformation results.

3. The specific procedure for transfection with the recombinant baculoviruspFastBac vector can be found in Xie et al. Expression of recombinant human soluble PDGFRβ/Fc in Sf9 insect cells. Entomological Journal. July 2009, 52(7): 743-748.

4. Expression of FGFR2b extracellular fragments

Supernatant and cells were collected and centrifuged at 16000 rpm and 4° C. Afterwards, the supernatant and cell pellet were subjected to SDS-PAGE electrophoresis and identified by Western Blot. The results show that FGFR2b extracellular fragment analogues can be specifically recognized by FGFR2b antibodies.

Example 6

Therapeutic Effects of 6 Types of FGFR2b Extracellular Fragments on Eczema

Figure 3:
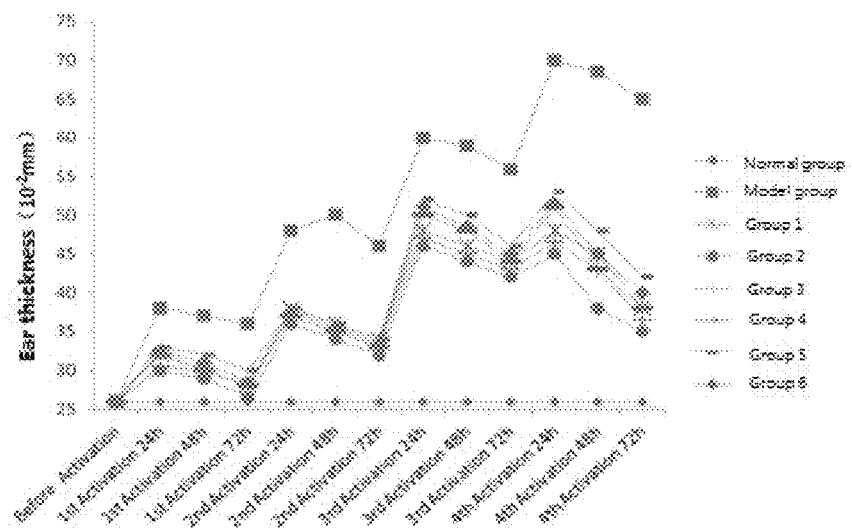
FIG. 3 shows the thickness of ear swelling of mice of each of the 6 types of FGFR2b extracellular fragments in each challenged stage according to Example 7. 1-3: wild-type, S252W mutant-type, and P253R mutant-type FGFR2b extracellular fragments of SEQ ID NO.8, 10, and 12, respectively; and 4-6: wild-type, S252W mutant-type, and P253R mutant-type FGFR2b extracellular fragments of SEQ ID NO.2, 4, and 6, respectively.

This example describes the therapeutic effects of the 6 types of FGFR2b extracellular fragments as listed in SEQ ID NO.2 and 8, SEQ ID NO.4 and 10 (S252W mutant type), and SEQ ID NO.6 and 12 (P253R mutant type), as prepared in accordance with Example 1, on eczema through experiments on mice, the experiment results of which are shown in FIG. 3.

I. Experimental Procedures 1. 80 clean-grade male ICR mice (provided by Laboratory animal center of SUN YAT-SEN University) were randomly divided into 8 groups based on their body weight: Normal group, Model group, and groups for each of the six types of FGFR2b extracellular fragment proteins, with 10 mice per group;

2. The mice, except for those of the Normal group, had their abdomen hair shaved and 100 μL of 1% 2,4-dinitrochlorobenzene (DNCB) in ethanol solution applied on the abdomen to cause allergy. After 5 days, the mice were challenged by applying 25 μL of 0.5% DNCB in ethanol solution uniformly on their left auriculaeonce every 3 days with a total of 4 times. The degree of mouse ear swelling was determined with a micrometer caliper after each challenge; and 3. A dose of 25 μL per mouse (a concentration of 100 ug/ml) was administrated to the mice in the groups for each of the three full-length FGFR2b extracellular fragment proteins, while a dose of 25 μL per mouse (a concentration of 50 ug/ml) was administrated to the mice in the groups for each of the three truncated FGFR2b extracellular fragment proteins, respectively, once per day (if on the day of challenge, then administrated 1 h before the challenge); and An equal volume of distilled water was given to the Normal group and the Model group continuously for 14 d.

II. Experimental Results

As shown in FIG. 3, as compared with the Normal group, the number of left ear scabs in the mice of the Model group was significantly increased. And as compared with the Model group, the numbers of left ear scabs in the mice of the six types of FGFR2b extracellular fragment proteins were significantly reduced, while the truncatedFGFR2b extracellular fragments had better effects relative to the full-length FGFR2b extracellular fragments.

Example 7

Therapeutic Effects of Six Types of FGFR2b Extracellular Fragments on Acnes

This experiment describes the therapeutic effects of the six types of FGFR2b extracellular fragments as listed in SEQ ID NO.2 and 8, SEQ ID NO.4 and 10 (S252W mutant type), and SEQ ID NO.6 and 12 (P253R mutant type), as prepared in accordance with Example 1, on acnes, including experiments for inhibiting keratinization and experiments for inhibiting sebaceous gland spots, the results of which are shown in Table 1 and 2.

I. The Experiment of FGFR2b Extracellular Fragment on Inhibiting Keratinization

1. Experimental Procedures (1). 48 male Japanese White Rabbits (with a body weight of 2~3 kg, provided by Laboratory animal center of SUN YAT-SEN University) were divided into the following groups: Normal Control group, Physiological Saline group, groups for each of the six types of FGFR2b extracellular fragments, with 6 rabbits per group in a total of 8 groups;

(2) Group 1 of 6 rabbits was the Normal Control group, without applying coal tar. The remaining 7 groups of 42 rabbits in total, were applied with 0.5 ml coal tar at the openings of the ear tubes inside both ears in a range of 2 cm×2 cm, once per day continuously for 2 weeks, to establish a rabbit ear experimental keratinization model;

(3) Administration phase:

Group 2 was the Physiological Saline group, to which 0.1 ml physiological saline was applied at the keratinization sites of both ears per day;

Groups 3-5 were the administration groups of the three truncated FGFR2b extracellular fragments, to which 0.1 ml of 50 μg/ml was applied at the keratinization sites of both ears per day;

Groups 6-8 were the administration groups of the three full-length FGFR2b extracellular fragments, to which 0.1 ml of 100 μg/ml was applied at the keratinization sites of both ears per day;

Each of the above mentioned groups was administrated twice per day continuously for 1 week.

(4). Determination indexes of the experimental effects

The histopathological changes of the specimens were classified into four grades according to increment in epidermis thickness, follicular orifice extension extent, and amount of the keratinized matter: 0 for no acnes, + for a small amount of the densified keratinized matter present at the hair follicular infundibulum site; ++ for a moderate amount of the keratinized matter present at the hair follicular infundibulum site, extending toward the sebaceous gland; and +++ for a large amount of the keratinized matter present in the dilated hair follicles.

2. Results

The experimental results were shown in Table 1. As compared with group 2, the keratinizations were significantly inhibited in Groups 3-8, wherein the truncated FGFR2b extracellular fragments had better effects than the full-length FGFR2b extracellular fragments.

TABLE 1

Effects of the FGFR extracellular fragments on the rabbit ear experimental keratinization model

| | | Histopathological change (grade) | | | P value Comparison with the |
|---|---|---|---|---|---|
| groups | n | 0 | + | ++ | Physiological Saline Group |
| 1 | 6 | 6 | 0 | 0 | <0.01 |
| 2 | 6 | 0 | 1 | 5 | |
| 3 | 6 | 3 | 3 | 0 | <0.01 |
| 4 | 6 | 5 | 1 | 0 | <0.01 |
| 5 | 6 | 4 | 2 | 0 | <0.01 |
| 6 | 6 | 1 | 5 | 0 | <0.01 |
| 7 | 6 | 3 | 3 | 0 | <0.01 |
| 8 | 6 | 2 | 4 | 0 | <0.01 |

II. Inhibition Experiment on Sebaceous Gland Spots by the FGFR2b Extracellular Fragments 1. Experimental Procedures:

(1). 56 adult male golden hamsters fed on standard diet in the environment at about 20° C. and used in the experiments after 2 weeks;

(2). The golden hamsters were depilated on the dorsal with depilatory agent to expose the sebaceous gland spots on both sides, and randomly divided into 7 groups including the Physiological Saline group and groups for each of the six types of FGFR2b extracellular fragments, with 8 hamsters per group;

(3) Administration Stage:

Group 1 was the Physiological Saline group (negative control group), to which 0.1 ml physiological saline was applied on the sebaceous gland spots on both sides;

Groups 2-4 were the administration groups for each of the three truncated FGFR2b extracellular fragments prepared by the same method as that described in example 2, to which 0.1 ml of 50 µg/ml was applied on the sebaceous gland spots on both sides;

Groups 5-7 were the administration groups for each of the three full-length FGFR2b extracellular fragments prepared by the same method as that described in example 2, to which 0.1 ml of 100 µg/ml was applied on the sebaceous gland spots on both sides;

Each of the above mentioned groups was administrated twice per day continuously for 30 days.

(4). Determination of Experimental Effects 24 h post the last administration, the golden hamsters of each group were anesthetized with diethyl ether, and the sebaceous gland spots on both sides were removed and observed for the histological changes under an optical microscope.

In a 40× view, each field of view was evenly divided into grids of 1 mm×1 mm. Number and area of grids occupied by the sebaceous gland in the field of view were calculated and compared among the groups (Redundant fields of view were removed during calculation). Determination of the thickness of the sebaceous gland: "thick" if the number of the overlapping gland lobes≥4; "moderate" if the number of the overlapping gland lobes was 2 or 3; and "thin" if the number of the gland lobe was 1.

2. Experimental Results

The experimental results were shown in Table 2. As compared with Group 2, the sebaceous gland spots were significantly inhibited in Groups 3 to 7, wherein the truncated FGFR2b extracellular fragments had better effects than the full-length FGFR2b extracellular fragments. P values were obtained by comparing each treatment group with the Control group.

Example 8

Determination of the Interactions Between Three Types of FGFR2b Extracellular Fragments and FGF7 by Isothermal Titration Calorimetry (iTC)

Figure 4:
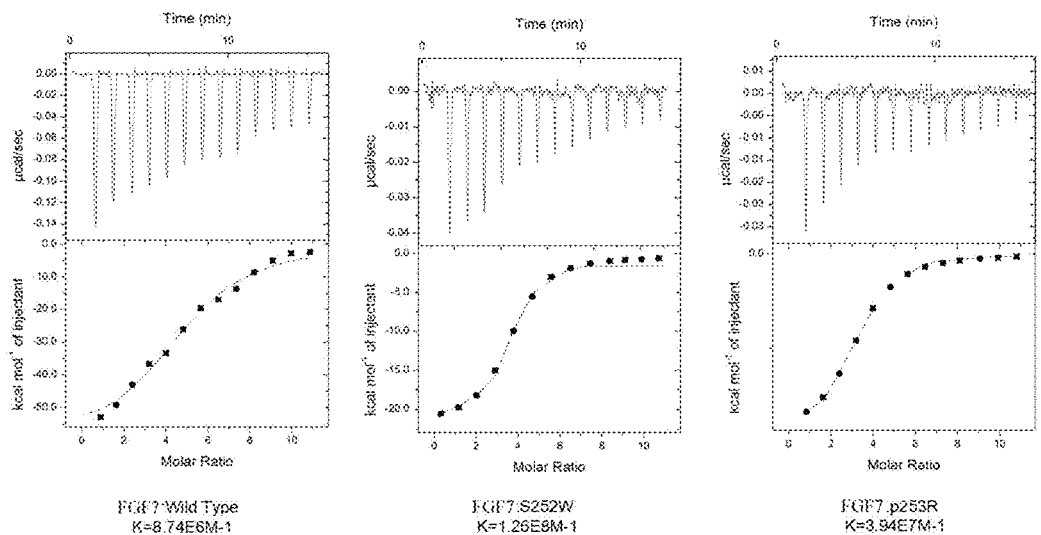
FIG. 4 shows the comparison of interaction between FGF7 and each of the three truncated FGFR2b extracellular fragments using isothermal titration calorimetry (ITC) according to Example 8. The samples are wild-type, S252W mutant-type, and P253R mutant-type FGFR2b extracellular fragments of SEQ ID NO.22, 24, and 26.

This experiment demonstrates the binding of the three types of truncated FGFR2b extracellular fragments listed in SEQ ID8, SEQ ID 10(S252W mutant type), and SEQ ID12(P253R mutant type) as prepared in accordance with the methods of Example 1 with FGF7(or KGF). The results are shown in FIG. 4.

The three types of the FGFR2b extracellular fragments and FGF7 (purchased from Millipore) were dialysed respectively with iTC buffer (0.15 mol/L NaCl and 5% glycerol in 20 mmol/L $Na_2HPO_4$-citrate buffer, pH 7.2). The proteins after the dialysis was centrifuged at 4° C. and 18000 rpm for 30 min before the iTC experiment.

400 ul 35 µmol/L of each of the three types of the FGFR2b extracellular fragments was added to the sample pool, respectively, and titrated with 200 µl 93 µmol/LFGF7 at 2 µl per time at a 2.5 min interval for a total of 20 drops.

The results demonstrated that the binding affinity of the S252W mutant-type and P253R mutant-type FGFR2b extracellular fragments were both stronger than the wild-type FGFR2b extracellular fragment.

Example 9

Figure 5:
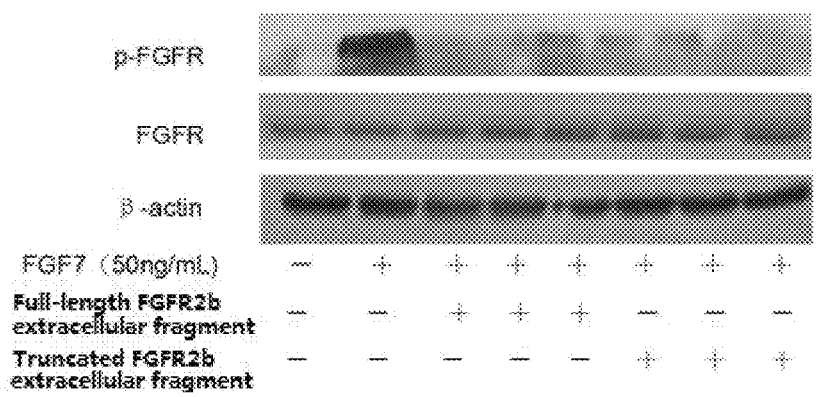
FIG. 5 shows the Western blotting analysis of 6 types of FGFR2b extracellular fragments which inhibit FGFR phosphorylation and block FGF signals by binding to ligand FGF7. The samples are wild-type, S252W mutant-type, and P253R mutant-type FGFR2b extracellular fragments of SEQ ID NO.2, 4, and 6, respectively; and wild-type, S252W mutant-type, and P253R mutant-type FGFR2b extracellular fragments of SEQ ID NO.8,10, and 12, respectively.

Examination of Inhibition of FGF Signal by Six Types of FGFR2b Extracellular Fragments Binding to Ligand This experiment demonstrates the six types of FGFR2b extracellular fragments listed in SEQ ID2 and 8, SEQ ID 4 and 10(S252W mutant type), and SEQ ID 6 and 12(P253R mutant type) as prepared in accordance with the methods of Example 1 bind with ligand to inhibit FGFR phosphorylation. The results are shown in FIG. 5.

1. Cell Culture

Human keratinocytesHacat (from ATCC) were passaged in a 50 $cm^2$ cell culture bottle (purchased from Thermo), added with MEM medium with 10% (v/v) fetal bovine serum, and incubated in a cell incubator at 37° C. and 5% $CO_2$.

2. Detection of FGFR2b Extracellular Fragment Binding with Ligand to Inhibit FGFR Phosphorylation by Western Blot The cells were incubated for 24 h and then washed with 1×PBS to remove the remaining medium, which was

TABLE 2

Effects of the FGFR extracellular fragment and the FGF7 antibody on the thickness and density of the sebaceous gland spots of the golden hamsters

| Groups | Thickness of the sebaceous gland spots | | | P value | Density of the sebaceous gland spots | | P value |
|---|---|---|---|---|---|---|---|
| | thick | moderate | thin | | dense | loose | |
| 1 | 4 | 3 | 1 | | 7 | 1 | |
| 2 | 2 | 2 | 4 | <0.01 | 3 | 5 | <0.01 |
| 3 | 0 | 2 | 6 | <0.01 | 1 | 7 | <0.01 |
| 4 | 0 | 3 | 5 | <0.01 | 2 | 6 | <0.01 |
| 5 | 1 | 4 | 3 | <0.01 | 2 | 6 | <0.01 |
| 6 | 0 | 3 | 5 | <0.01 | 3 | 5 | <0.01 | replaced with MEM starve medium with 0.5%(v/v) FBS. Induction was performed after 12 h. The specific procedures were as follows: 3%(v/v) FBS MEM medium containing 50 ng/ml FGF7(or called KGF) or 1 ug/ml of the six types of FGFR2b extracellular fragments was transferred to a 6-well plate with 2 ml per well;

Well #1: addition of 3%(v/v)FBS MEM medium;
Well #2: addition of 3%(v/v)FBS MEM medium+FGF7;
Wells #3-5: addition of 3%(v/v)FBS MEM medium+the three types of the full-length FGFR2b extracellular fragments +FGF7;
Wells #6-8: addition of 3%(v/v)FBS MEM medium+the three types of the truncated FGFR2b extracellular fragments +FGF7.

Western Blot analysis was conducted 1 h post induction. All the antibodies applied were purchased from CST and FGF7 was purchased from Millipore.

FGF7 actives the FGF signal by inducing the autophosphorylation of FGFR2b. In the Western Blot analysis, anti-phosphorylated-FGFR antibodies were used, and the amount of the phosphorylated FGFR was sufficient for FGF signal activation. With the effect of FGF7, there was plenty of FGFR phosphorylated (Lane 2 counting from the left), while the significant decrease in phosphorylated FGFR indicated that the activation effect of FGF7 was inhibited by the FGFR2b extracellular fragments (Lanes 3-8 counting from the left).

The detailed embodiments described herein are only for the purpose of illustrating the present disclosure, and are not intended to limit the scope of the present disclosure in any way. It would be understand by a person skilled in the art that various changes and modifications can be made to the embodiments described herein without departing from the scope and spirit of the present disclosure. Such changes and modifications are contemplated by the present disclosure, the scope of which should only be defined by the following claims.

The invention claimed is:

1. An isolated protein consisting of an amino acid sequence selected from the group consisting of:

i) amino acid sequences listed in SEQ ID NO : 2, 4, 6, 8, 10, or 12.

* * * * *

SEQUENCE LISTING

```
<160> NUMBER OF SEQ ID NOS: 32

<210> SEQ ID NO 1
<211> LENGTH: 738
<212> TYPE: DNA
<213> ORGANISM: Artificial Sequence
<220> FEATURE:
<223> OTHER INFORMATION: FGFR2b extracellular fragment

<400> SEQUENCE: 1
gcaccatact ggaccaacac agaaaagatg gaaaagcggc tccatgctgt gcctgcggcc      60
aacactgtca agtttcgctg cccagccggg gggaacccaa tgccaaccat gcggtggctg     120
aaaaacggga aggagtttaa gcaggagcat cgcattggag gctacaaggt acgaaaccag     180
cactggagcc tcattatgga aagtgtggtc ccatctgaca agggaaatta tacctgtgtg     240
gtggagaatg aatacgggtc catcaatcac acgtaccacc tggatgttgt ggagcgatcg     300
cctcaccggc ccatcctcca agccggactg ccggcaaatg cctccacagt ggtcggagga     360
gacgtagagt ttgtctgcaa ggtttacagt gatgcccagc cccacatcca gtggatcaag     420
cacgtggaaa agaacggcag taaatacggg cccgacgggc tgccctacct caaggttctc     480
aagcactcgg ggataaatag ttccaatgca gaagtgctgg ctctgttcaa tgtgaccgag     540
gcggatgctg gggaatatat atgtaaggtc tccaattata tagggcaggc caaccagtct     600
gcctggctca ctgtcctgcc aaaacagcaa gcgcctggaa gagaaaagga gattacagct     660
tccccagact acctggagat agccatttac tgcataggg  tcttcttaat cgcctgtatg     720
gtggtaacag tcatcctg                                                  738

<210> SEQ ID NO 2
<211> LENGTH: 246
<212> TYPE: PRT
<213> ORGANISM: Artificial Sequence
<220> FEATURE:
<223> OTHER INFORMATION: FGFR2b extracellular fragment

<400> SEQUENCE: 2

Ala Pro Tyr Trp Thr Asn Thr Glu Lys Met Glu Lys Arg Leu His Ala
 1               5                  10                  15

Val Pro Ala Ala Asn Thr Val Lys Phe Arg Cys Pro Ala Gly Gly Asn
            20                  25                  30

Pro Met Pro Thr Met Arg Trp Leu Lys Asn Gly Lys Glu Phe Lys Gln
```

```
                35                  40                  45
Glu His Arg Ile Gly Gly Tyr Lys Val Arg Asn Gln His Trp Ser Leu
 50                  55                  60
Ile Met Glu Ser Val Val Pro Ser Asp Lys Gly Asn Tyr Thr Cys Val
 65                  70                  75                  80
Val Glu Asn Glu Tyr Gly Ser Ile Asn His Thr Tyr His Leu Asp Val
                 85                  90                  95
Val Glu Arg Ser Pro His Arg Pro Ile Leu Gln Ala Gly Leu Pro Ala
                100                 105                 110
Asn Ala Ser Thr Val Val Gly Gly Asp Val Glu Phe Val Cys Lys Val
                115                 120                 125
Tyr Ser Asp Ala Gln Pro His Ile Gln Trp Ile Lys His Val Glu Lys
                130                 135                 140
Asn Gly Ser Lys Tyr Gly Pro Asp Gly Leu Pro Tyr Leu Lys Val Leu
145                 150                 155                 160
Lys His Ser Gly Ile Asn Ser Ser Asn Ala Glu Val Leu Ala Leu Phe
                165                 170                 175
Asn Val Thr Glu Ala Asp Ala Gly Glu Tyr Ile Cys Lys Val Ser Asn
                180                 185                 190
Tyr Ile Gly Gln Ala Asn Gln Ser Ala Trp Leu Thr Val Leu Pro Lys
                195                 200                 205
Gln Gln Ala Pro Gly Arg Glu Lys Glu Ile Thr Ala Ser Pro Asp Tyr
                210                 215                 220
Leu Glu Ile Ala Ile Tyr Cys Ile Gly Val Phe Leu Ile Ala Cys Met
225                 230                 235                 240
Val Val Thr Val Ile Leu
                245

<210> SEQ ID NO 3
<211> LENGTH: 738
<212> TYPE: DNA
<213> ORGANISM: Artificial Sequence
<220> FEATURE:
<223> OTHER INFORMATION: FGFR2b extracellular fragment

<400> SEQUENCE: 3
gcaccatact ggaccaacac agaaaagatg gaaaagcggc tccatgctgt gcctgcggcc      60
aacactgtca gtttcgctg cccagccggg gggaacccaa tgccaaccat gcggtggctg     120
aaaaacggga aggagtttaa gcaggagcat cgcattggag gctacaaggt acgaaaccag    180
cactggagcc tcattatgga aagtgtggtc ccatctgaca agggaaatta tacctgtgtg    240
gtggagaatg aatacgggtc catcaatcac acgtaccacc tggatgttgt ggagcgatgg    300
cctcaccggc ccatcctcca agccggactg ccggcaaatg cctccacagt ggtcggagga    360
gacgtagagt ttgtctgcaa ggtttacagt gatgcccagc ccacatcca gtggatcaag    420 cacgtggaaa agaacggcag taaatacggg cccgacgggc tgccctacct caaggttctc    480
aagcactcgg gataaatag ttccaatgca gaagtgctgg ctctgttcaa tgtgaccgag    540
gcggatgctg gggaatatat atgtaaggtc tccaattata tagggcaggc caaccagtct    600
gcctggctca ctgtcctgcc aaaacagcaa gcgcctggaa gagaaaagga gattacagct    660
tccccagact acctggagat agccatttac tgcataggg tcttcttaat cgcctgtatg    720
gtggtaacag tcatcctg                                                    738

<210> SEQ ID NO 4
```

<211> LENGTH: 246
<212> TYPE: PRT
<213> ORGANISM: Artificial Sequence
<220> FEATURE:
<223> OTHER INFORMATION: FGFR2b extracellular fragment

<400> SEQUENCE: 4

```
Ala Pro Tyr Trp Thr Asn Thr Glu Lys Met Glu Lys Arg Leu His Ala
1               5                   10                  15

Val Pro Ala Ala Asn Thr Val Lys Phe Arg Cys Pro Ala Gly Gly Asn
            20                  25                  30

Pro Met Pro Thr Met Arg Trp Leu Lys Asn Gly Lys Glu Phe Lys Gln
        35                  40                  45

Glu His Arg Ile Gly Gly Tyr Lys Val Arg Asn Gln His Trp Ser Leu
    50                  55                  60

Ile Met Glu Ser Val Val Pro Ser Asp Lys Gly Asn Tyr Thr Cys Val
65                  70                  75                  80

Val Glu Asn Glu Tyr Gly Ser Ile Asn His Thr Tyr His Leu Asp Val
                85                  90                  95

Val Glu Arg Trp Pro His Arg Pro Ile Leu Gln Ala Gly Leu Pro Ala
            100                 105                 110

Asn Ala Ser Thr Val Val Gly Gly Asp Val Glu Phe Val Cys Lys Val
        115                 120                 125

Tyr Ser Asp Ala Gln Pro His Ile Gln Trp Ile Lys His Val Glu Lys
    130                 135                 140

Asn Gly Ser Lys Tyr Gly Pro Asp Gly Leu Pro Tyr Leu Lys Val Leu
145                 150                 155                 160

Lys His Ser Gly Ile Asn Ser Ser Asn Ala Glu Val Leu Ala Leu Phe
                165                 170                 175

Asn Val Thr Glu Ala Asp Ala Gly Glu Tyr Ile Cys Lys Val Ser Asn
            180                 185                 190

Tyr Ile Gly Gln Ala Asn Gln Ser Ala Trp Leu Thr Val Leu Pro Lys
        195                 200                 205

Gln Gln Ala Pro Gly Arg Glu Lys Glu Ile Thr Ala Ser Pro Asp Tyr
    210                 215                 220

Leu Glu Ile Ala Ile Tyr Cys Ile Gly Val Phe Leu Ile Ala Cys Met
225                 230                 235                 240

Val Val Thr Val Ile Leu
                245
```

<210> SEQ ID NO 5
<211> LENGTH: 738
<212> TYPE: DNA
<213> ORGANISM: Artificial Sequence
<220> FEATURE:
<223> OTHER INFORMATION: FGFR2b extracellular fragment

<400> SEQUENCE: 5

| | | |
|---|---|---|
| gcaccatact ggaccaacac agaaaagatg gaaaagcggc tccatgctgt gcctgcggcc | 60 |
| aacactgtca gtttcgctgc ccagccgggg ggaacccaa tgccaaccat gcggtggctg | 120 |
| aaaaacggga aggagtttaa gcaggagcat cgcattggag gctacaaggt acgaaaccag | 180 |
| cactggagcc tcattatgga aagtgtggtc ccatctgaca agggaaatta tacctgtgtg | 240 |
| gtggagaatg aatacgggtc catcaatcac acgtaccacc tggatgttgt ggagcgatcg | 300 |
| cgtcaccggc ccatcctcca agccggactg ccggcaaatg cctccacagt ggtcggagga | 360 |
| gacgtagagt ttgtctgcaa ggtttacagt gatgcccagc ccacatcca gtggatcaag | 420 |

```
cacgtggaaa agaacggcag taaatacggg cccgacgggc tgccctacct caaggttctc    480
aagcactcgg ggataaatag ttccaatgca gaagtgctgg ctctgttcaa tgtgaccgag    540
gcggatgctg gggaatatat atgtaaggtc tccaattata tagggcaggc caaccagtct    600
gcctggctca ctgtcctgcc aaaacagcaa gcgcctggaa gagaaaagga gattacagct    660
tccccagact acctggagat agccatttac tgcataggggg tcttcttaat cgcctgtatg    720
gtggtaacag tcatcctg                                                  738
```

<210> SEQ ID NO 6
<211> LENGTH: 246
<212> TYPE: PRT
<213> ORGANISM: Artificial Sequence
<220> FEATURE:
<223> OTHER INFORMATION: FGFR2b extracellular fragment

<400> SEQUENCE: 6

```
Ala Pro Tyr Trp Thr Asn Thr Glu Lys Met Glu Lys Arg Leu His Ala
  1               5                  10                  15

Val Pro Ala Ala Asn Thr Val Lys Phe Arg Cys Pro Ala Gly Gly Asn
             20                  25                  30

Pro Met Pro Thr Met Arg Trp Leu Lys Asn Gly Lys Glu Phe Lys Gln
         35                  40                  45

Glu His Arg Ile Gly Gly Tyr Lys Val Arg Asn Gln His Trp Ser Leu
     50                  55                  60

Ile Met Glu Ser Val Val Pro Ser Asp Lys Gly Asn Tyr Thr Cys Val
 65                  70                  75                  80

Val Glu Asn Glu Tyr Gly Ser Ile Asn His Thr Tyr His Leu Asp Val
                 85                  90                  95

Val Glu Arg Ser Arg His Arg Pro Ile Leu Gln Ala Gly Leu Pro Ala
            100                 105                 110

Asn Ala Ser Thr Val Val Gly Gly Asp Val Glu Phe Val Cys Lys Val
        115                 120                 125

Tyr Ser Asp Ala Gln Pro His Ile Gln Trp Ile Lys His Val Glu Lys
    130                 135                 140

Asn Gly Ser Lys Tyr Gly Pro Asp Gly Leu Pro Tyr Leu Lys Val Leu
145                 150                 155                 160

Lys His Ser Gly Ile Asn Ser Ser Asn Ala Glu Val Leu Ala Leu Phe
                165                 170                 175

Asn Val Thr Glu Ala Asp Ala Gly Glu Tyr Ile Cys Lys Val Ser Asn
            180                 185                 190

Tyr Ile Gly Gln Ala Asn Gln Ser Ala Trp Leu Thr Val Leu Pro Lys
        195                 200                 205

Gln Gln Ala Pro Gly Arg Glu Lys Glu Ile Thr Ala Ser Pro Asp Tyr
    210                 215                 220

Leu Glu Ile Ala Ile Tyr Cys Ile Gly Val Phe Leu Ile Ala Cys Met
225                 230                 235                 240

Val Val Thr Val Ile Leu
                245
```

<210> SEQ ID NO 7
<211> LENGTH: 648
<212> TYPE: DNA
<213> ORGANISM: Artificial Sequence
<220> FEATURE:
<223> OTHER INFORMATION: TRUNCATED WILD TYPE

<400> SEQUENCE: 7

```
aagagagcac catactggac caacacagaa aagatggaaa agcggctcca tgctgtgcct      60
gcggccaaca ctgtcaagtt tcgctgccca gccgggggga acccaatgcc aaccatgcgg     120
tggctgaaaa acgggaagga gtttaagcag gagcatcgca ttggaggcta caaggtacga     180
aaccagcact ggagcctcat tatggaaagt gtggtcccat ctgacaaggg aaattatacc     240
tgtgtagtgg agaatgaata cgggtccatc aatcacacgt accacctgga tgttgtggag     300
cgatcgcctc accggcccat cctccaagcc ggactgccgg caaatgcctc cacagtggtc     360
ggaggagacg tagagtttgt ctgcaaggtt tacagtgatg cccagcccca catccagtgg     420
atcaagcacg tggaaaagaa cggcagtaaa tacgggcccg acgggctgcc ctacctcaag     480
gttctcaagc actcggggat aaatagttcc aatgcagaag tgctggctct gttcaatgtg     540
accgaggcgg atgctgggga atatatatgt aaggtctcca attatatagg gcaggccaac     600
cagtctgcct ggctcactgt cctgccaaaa cagcaagcgc tggaaga                   648
```

<210> SEQ ID NO 8
<211> LENGTH: 216
<212> TYPE: PRT
<213> ORGANISM: Artificial Sequence
<220> FEATURE:
<223> OTHER INFORMATION: TRUNCATED WILD TYPE

<400> SEQUENCE: 8

```
Lys Arg Ala Pro Tyr Trp Thr Asn Thr Glu Lys Met Glu Lys Arg Leu
1               5                   10                  15

His Ala Val Pro Ala Ala Asn Thr Val Lys Phe Arg Cys Pro Ala Gly
                20                  25                  30

Gly Asn Pro Met Pro Thr Met Arg Trp Leu Lys Asn Gly Lys Glu Phe
            35                  40                  45

Lys Gln Glu His Arg Ile Gly Gly Tyr Lys Val Arg Asn Gln His Trp
        50                  55                  60

Ser Leu Ile Met Glu Ser Val Val Pro Ser Asp Lys Gly Asn Tyr Thr
65                  70                  75                  80

Cys Val Val Glu Asn Glu Tyr Gly Ser Ile Asn His Thr Tyr His Leu
                85                  90                  95

Asp Val Val Glu Arg Ser Pro His Arg Pro Ile Leu Gln Ala Gly Leu
                100                 105                 110

Pro Ala Asn Ala Ser Thr Val Val Gly Gly Asp Val Glu Phe Val Cys
            115                 120                 125

Lys Val Tyr Ser Asp Ala Gln Pro His Ile Gln Trp Ile Lys His Val
        130                 135                 140

Glu Lys Asn Gly Ser Lys Tyr Gly Pro Asp Gly Leu Pro Tyr Leu Lys
145                 150                 155                 160

Val Leu Lys His Ser Gly Ile Asn Ser Ser Asn Ala Glu Val Leu Ala
                165                 170                 175

Leu Phe Asn Val Thr Glu Ala Asp Ala Gly Glu Tyr Ile Cys Lys Val
                180                 185                 190

Ser Asn Tyr Ile Gly Gln Ala Asn Gln Ser Ala Trp Leu Thr Val Leu
            195                 200                 205

Pro Lys Gln Gln Ala Pro Gly Arg
        210                 215
```

<210> SEQ ID NO 9
<211> LENGTH: 648

<212> TYPE: DNA
<213> ORGANISM: Artificial Sequence
<220> FEATURE:
<223> OTHER INFORMATION: TRUNCATED 252 MUTANT-TYPE BASE SEQUENCE

<400> SEQUENCE: 9

```
aagagagcac catactggac caacacagaa aagatggaaa agcggctcca tgctgtgcct      60
gcggccaaca ctgtcaagtt tcgctgccca gccgggggga acccaatgcc aaccatgcgg     120
tggctgaaaa acgggaagga gtttaagcag gagcatcgca ttggaggcta caaggtacga     180
aaccagcact ggagcctcat tatggaaagt gtggtcccat ctgacaaggg aaattatacc     240
tgtgtagtgg agaatgaata cgggtccatc aatcacacgt accacctgga tgttgtggag     300
cgatggcctc accggcccat cctccaagcc ggactgccgg caaatgcctc cacagtggtc     360
ggaggagacg tagagtttgt ctgcaaggtt tacagtgatg cccagcccca catccagtgg     420
atcaagcacg tggaaaagaa cggcagtaaa tacgggcccg acgggctgcc ctacctcaag     480
gttctcaagc actcggggat aaatagttcc aatgcagaag tgctggctct gttcaatgtg     540
accgaggcgg atgctgggga atatatatgt aaggtctcca attatatagg gcaggccaac     600
cagtctgcct ggctcactgt cctgccaaaa cagcaagcgc ctggaaga                  648
```

<210> SEQ ID NO 10
<211> LENGTH: 216
<212> TYPE: PRT
<213> ORGANISM: Artificial Sequence
<220> FEATURE:
<223> OTHER INFORMATION: TRUNCATED 252 MUTANT-TYPE AMINO ACID SEQUENCE

<400> SEQUENCE: 10

```
Lys Arg Ala Pro Tyr Trp Thr Asn Thr Glu Lys Met Glu Lys Arg Leu
1               5                   10                  15

His Ala Val Pro Ala Ala Asn Thr Val Lys Phe Arg Cys Pro Ala Gly
                20                  25                  30

Gly Asn Pro Met Pro Thr Met Arg Trp Leu Lys Asn Gly Lys Glu Phe
            35                  40                  45

Lys Gln Glu His Arg Ile Gly Gly Tyr Lys Val Arg Asn Gln His Trp
        50                  55                  60

Ser Leu Ile Met Glu Ser Val Val Pro Ser Asp Lys Gly Asn Tyr Thr
65                  70                  75                  80

Cys Val Val Glu Asn Glu Tyr Gly Ser Ile Asn His Thr Tyr His Leu
                85                  90                  95

Asp Val Val Glu Arg Trp Pro His Arg Pro Ile Leu Gln Ala Gly Leu
            100                 105                 110

Pro Ala Asn Ala Ser Thr Val Val Gly Gly Asp Val Glu Phe Val Cys
        115                 120                 125

Lys Val Tyr Ser Asp Ala Gln Pro His Ile Gln Trp Ile Lys His Val
    130                 135                 140

Glu Lys Asn Gly Ser Lys Tyr Gly Pro Asp Gly Leu Pro Tyr Leu Lys
145                 150                 155                 160

Val Leu Lys His Ser Gly Ile Asn Ser Ser Asn Ala Glu Val Leu Ala
                165                 170                 175

Leu Phe Asn Val Thr Glu Ala Asp Ala Gly Glu Tyr Ile Cys Lys Val
            180                 185                 190

Ser Asn Tyr Ile Gly Gln Ala Asn Gln Ser Ala Trp Leu Thr Val Leu
        195                 200                 205

Pro Lys Gln Gln Ala Pro Gly Arg
    210                 215
```

<210> SEQ ID NO 11
<211> LENGTH: 648
<212> TYPE: DNA
<213> ORGANISM: Artificial Sequence
<220> FEATURE:
<223> OTHER INFORMATION: TRUNCATED 253 MUTANT-TYPE BASE SEQUENCE

<400> SEQUENCE: 11

```
aagagagcac catactggac caacacagaa aagatggaaa agcggctcca tgctgtgcct      60
gcggccaaca ctgtcaagtt tcgctgccca gccgggggga acccaatgcc aaccatgcgg     120
tggctgaaaa acgggaagga gtttaagcag gagcatcgca ttggaggcta caaggtacga     180
aaccagcact ggagcctcat tatggaaagt gtggtcccat ctgacaaggg aaattatacc     240
tgtgtagtgg agaatgaata cgggtccatc aatcacacgt accacctgga tgttgtggag     300
cgatcgcgtc accggcccat cctccaagcc ggactgccgg caaatgcctc cacagtggtc     360
ggaggagacg tagagtttgt ctgcaaggtt tacagtgatg cccagcccca catccagtgg     420
atcaagcacg tggaaaagaa cggcagtaaa tacgggcccg acgggctgcc ctacctcaag     480
gttctcaagc actcggggat aaatagttcc aatgcagaag tgctggctct gttcaatgtg     540
accgaggcgg atgctgggga atatatatgt aaggtctcca attatatagg gcaggccaac     600
cagtctgcct ggctcactgt cctgccaaaa cagcaagcgc tggaaga                  648
```

<210> SEQ ID NO 12
<211> LENGTH: 216
<212> TYPE: PRT
<213> ORGANISM: Artificial Sequence
<220> FEATURE:
<223> OTHER INFORMATION: TRUNCATED 252 MUTANT-TYPE AMINO ACID SEQUENCE

<400> SEQUENCE: 12

```
Lys Arg Ala Pro Tyr Trp Thr Asn Thr Glu Lys Met Glu Lys Arg Leu
1               5                   10                  15

His Ala Val Pro Ala Ala Asn Thr Val Lys Phe Arg Cys Pro Ala Gly
            20                  25                  30

Gly Asn Pro Met Pro Thr Met Arg Trp Leu Lys Asn Gly Lys Glu Phe
        35                  40                  45

Lys Gln Glu His Arg Ile Gly Gly Tyr Lys Val Arg Asn Gln His Trp
    50                  55                  60

Ser Leu Ile Met Glu Ser Val Val Pro Ser Asp Lys Gly Asn Tyr Thr
65                  70                  75                  80

Cys Val Val Glu Asn Glu Tyr Gly Ser Ile Asn His Thr Tyr His Leu
                85                  90                  95

Asp Val Val Glu Arg Ser Arg His Arg Pro Ile Leu Gln Ala Gly Leu
            100                 105                 110

Pro Ala Asn Ala Ser Thr Val Val Gly Gly Asp Val Glu Phe Val Cys
        115                 120                 125

Lys Val Tyr Ser Asp Ala Gln Pro His Ile Gln Trp Ile Lys His Val
    130                 135                 140

Glu Lys Asn Gly Ser Lys Tyr Gly Pro Asp Gly Leu Pro Tyr Leu Lys
145                 150                 155                 160

Val Leu Lys His Ser Gly Ile Asn Ser Ser Asn Ala Glu Val Leu Ala
                165                 170                 175

Leu Phe Asn Val Thr Glu Ala Asp Ala Gly Glu Tyr Ile Cys Lys Val
            180                 185                 190
```

```
Ser Asn Tyr Ile Gly Gln Ala Asn Gln Ser Ala Trp Leu Thr Val Leu
    195                 200                 205

Pro Lys Gln Gln Ala Pro Gly Arg
    210                 215
```

```
<210> SEQ ID NO 13
<211> LENGTH: 26
<212> TYPE: DNA
<213> ORGANISM: Artificial Sequence
<220> FEATURE:
<223> OTHER INFORMATION: Primer F1

<400> SEQUENCE: 13
cgcatatggc accatactgg accaac                                          26

<210> SEQ ID NO 14
<211> LENGTH: 32
<212> TYPE: DNA
<213> ORGANISM: Artificial Sequence
<220> FEATURE:
<223> OTHER INFORMATION: Primer R1

<400> SEQUENCE: 14
atggatccct attacaggat gactgttacc ac                                   32

<210> SEQ ID NO 15
<211> LENGTH: 26
<212> TYPE: DNA
<213> ORGANISM: Artificial Sequence
<220> FEATURE:
<223> OTHER INFORMATION: Primer F1'

<400> SEQUENCE: 15
cgcatatgaa gagagcacca tactgg                                          26

<210> SEQ ID NO 16
<211> LENGTH: 32
<212> TYPE: DNA
<213> ORGANISM: Artificial Sequence
<220> FEATURE:
<223> OTHER INFORMATION: Primer R1'

<400> SEQUENCE: 16
atggatccct attatcttcc aggcgcttgc tg                                   32

<210> SEQ ID NO 17
<211> LENGTH: 28
<212> TYPE: DNA
<213> ORGANISM: Artificial Sequence
<220> FEATURE:
<223> OTHER INFORMATION: Primer F2

<400> SEQUENCE: 17
ttgtggagcg atggcctcac cggcccat                                        28

<210> SEQ ID NO 18
<211> LENGTH: 28
<212> TYPE: DNA
<213> ORGANISM: Artificial Sequence
<220> FEATURE:
<223> OTHER INFORMATION: Primer R2

<400> SEQUENCE: 18
atgggccggt gaggccatcg ctccacaa                                        28
```

<210> SEQ ID NO 19
<211> LENGTH: 27
<212> TYPE: DNA
<213> ORGANISM: Artificial Sequence
<220> FEATURE:
<223> OTHER INFORMATION: Primer F3

<400> SEQUENCE: 19
ttgtggagcg atcgcgtcac cgcccat                                        27

<210> SEQ ID NO 20
<211> LENGTH: 27
<212> TYPE: DNA
<213> ORGANISM: Artificial Sequence
<220> FEATURE:
<223> OTHER INFORMATION: Primer R3

<400> SEQUENCE: 20
atgggcggtg acgcgatcgc tccacaa                                        27

<210> SEQ ID NO 21
<211> LENGTH: 40
<212> TYPE: DNA
<213> ORGANISM: Artificial Sequence
<220> FEATURE:
<223> OTHER INFORMATION: Primer F4

<400> SEQUENCE: 21
atatggatcc gccgccacca tggcaccata ctggaccaac                          40

<210> SEQ ID NO 22
<211> LENGTH: 34
<212> TYPE: DNA
<213> ORGANISM: Artificial Sequence
<220> FEATURE:
<223> OTHER INFORMATION: Primer R4

<400> SEQUENCE: 22
gcgcaagctt tcattacagg atgactgtta ccac                                34

<210> SEQ ID NO 23
<211> LENGTH: 40
<212> TYPE: DNA
<213> ORGANISM: Artificial Sequence
<220> FEATURE:
<223> OTHER INFORMATION: Primer F4'

<400> SEQUENCE: 23
atatggatcc gccgccacca tgaagagagc accatactgg                          40

<210> SEQ ID NO 24
<211> LENGTH: 34
<212> TYPE: DNA
<213> ORGANISM: Artificial Sequence
<220> FEATURE:
<223> OTHER INFORMATION: Primer R4'

<400> SEQUENCE: 24
gcgcaagctt tcattatctt ccaggcgctt gctg                                34

<210> SEQ ID NO 25
<211> LENGTH: 40
<212> TYPE: DNA
<213> ORGANISM: Artificial Sequence
<220> FEATURE:
<223> OTHER INFORMATION: Primer F5

```
<400> SEQUENCE: 25
atatgaattc gccgccacca tggcaccata ctggaccaac                              40

<210> SEQ ID NO 26
<211> LENGTH: 34
<212> TYPE: DNA
<213> ORGANISM: Artificial Sequence
<220> FEATURE:
<223> OTHER INFORMATION: Primer R5

<400> SEQUENCE: 26
gcgcggatcc tcattacagg atgactgtta ccac                                   34

<210> SEQ ID NO 27
<211> LENGTH: 40
<212> TYPE: DNA
<213> ORGANISM: Artificial Sequence
<220> FEATURE:
<223> OTHER INFORMATION: Primer F5'

<400> SEQUENCE: 27
atatgaattc gccgccacca tgaagagagc accatactgg                             40

<210> SEQ ID NO 28
<211> LENGTH: 34
<212> TYPE: DNA
<213> ORGANISM: Artificial Sequence
<220> FEATURE:
<223> OTHER INFORMATION: Primer R5'

<400> SEQUENCE: 28
gcgcggatcc tcattatctt ccaggcgctt gctg                                   34

<210> SEQ ID NO 29
<211> LENGTH: 40
<212> TYPE: DNA
<213> ORGANISM: Artificial Sequence
<220> FEATURE:
<223> OTHER INFORMATION: Primer F6

<400> SEQUENCE: 29
atatctcgag gccgccacca tggcaccata ctggaccaac                             40

<210> SEQ ID NO 30
<211> LENGTH: 35
<212> TYPE: DNA
<213> ORGANISM: Artificial Sequence
<220> FEATURE:
<223> OTHER INFORMATION: Primer R6

<400> SEQUENCE: 30
gcgctctaga tcattacagg atgactgtta ccacc                                  35

<210> SEQ ID NO 31
<211> LENGTH: 40
<212> TYPE: DNA
<213> ORGANISM: Artificial Sequence
<220> FEATURE:
<223> OTHER INFORMATION: Primer F6'

<400> SEQUENCE: 31
atatctcgag gccgccacca tgaagagagc accatactgg                             40

<210> SEQ ID NO 32
```

```
<211> LENGTH: 34
<212> TYPE: DNA
<213> ORGANISM: Artificial Sequence
<220> FEATURE:
<223> OTHER INFORMATION: Primer R6'

<400> SEQUENCE: 32
gcgctctaga tcattatctt ccaggcgctt gctg                           34
```